United States Patent [19]

Thornfeldt

[11] Patent Number: 5,057,501

[45] Date of Patent: * Oct. 15, 1991

[54] METHODS FOR TREATMENT OF PAPULOSQUAMOUS AND ECZEMATOUS DISEASES

[75] Inventor: Carl R. Thornfeldt, Ontario, Oreg.

[73] Assignee: Dermatologic Research Corporation, Napa, Calif.

[*] Notice: The portion of the term of this patent subsequent to Dec. 18, 2007 has been disclaimed.

[21] Appl. No.: 492,690

[22] Filed: Mar. 13, 1990

[51] Int. Cl.$^5$ .................. A61K 31/335; A61K 31/715
[52] U.S. Cl. ..................................... 514/53; 514/450; 514/861; 514/863; 514/864
[58] Field of Search ................ 514/450, 53, 863, 864, 514/867

[56] References Cited

U.S. PATENT DOCUMENTS 3,535,422 10/1970 Cox et al. ............................. 424/164
4,978,676 12/1990 Thornfeldt ........................... 514/450

OTHER PUBLICATIONS

Who, "The Development of Artemisinin And Its Derivatives: Report of a Meeting of the Scientific Working Group on the Chemotherapy of Malaria", Geneva, 6–7 Oct. 1986.

D. L. Klayman, "Qinghaosu (Artemisinin): An Antimalarial Drug from China", *Science*, vol. 228, 31 May 1985.

Krungkrai, S. R. et al., "The Antimalarial Action of Plasmodium Falciparum of Qinghaosu and Artesunate in Combination with Agents which Modulate Oxidant Stress", Transactions of The Royal Society of Tropical Medicine and Hygiene (1987), 81, 710–714.

*Primary Examiner*—Leonard Schenkman
*Attorney, Agent, or Firm*—Townsend and Townsend

[57] ABSTRACT

Certain compounds having sesquiterpene structures, when combined with monocarboxylic fatty acids, esters or amides, have efficacy in the treatment of papulosquamous and eczematous diseases. Prime examples of the sesquiterpene compounds are artemisinin and analogs, and prime examples of the monocarboxylic fatty acid compounds are lauric acid, monolaurin and lauryl-N,N-dimethylamide.

21 Claims, No Drawings

METHODS FOR TREATMENT OF PAPULOSQUAMOUS AND ECZEMATOUS DISEASES

BACKGROUND OF THE INVENTION

This invention lies in the field of systemic and topical treatments of papulosquamous diseases and eczematous diseases.

Papulosquamous diseases are those conditions of the skin characterized by sharply demarcated red scaley patches or plaques that microscopically display acanthosis and hyperkeratosis without spongiosis. Inflammation and hyperproliferation are the key pathophysiologic processes in these diseases. Included among this group of diseases are psoriasis, lichen planus, pityriasis and parapsoriasis.

Eczematous diseases are those inflammatory skin conditions characterized by poorly demarcated scaley, crusty or weeping patches that microscopically display spongiosis. This group of diseases includes seborrheic and atopic dermatitis, contact allergic and irritant dermatitis, dyshidrosis, lichen simplex chronicus, eczema craquelé, and patch and plaque stages of cutaneous T cell lymphoma.

Microbial infection by bacteria, fungus or yeast often aggravate, and occasionally cause, the eruption of diseases within both groups. Such organisms also retard therapeutic response.

Various therapeutic formulations for papulosquamous and eczematous diseases are commercially available.

One type of available formulation utilizes the class of compounds known as glucocorticosteroids. These are derivatives of cholesterol which are antiinflammatory and mildly antiproliferative. Despite their status as the mainstay of treatment for these diseases, however, these agents give rise to numerous adverse reactions when used systemically or topically, some of which are irreversible.

Another type are chemotherapeutic compounds, including antimetabolites such as methotrexate and fluorouracil, alkylating agents such as mechlorethamine and carmustine, antibiotics such as bleomycin, and immunosuppressives such as cyclosporin, dapsone and colchicine.

Certain retinoids have proven efficacy against papulosquamous diseases. These include isotretinoin, tretinoin, etretinate and etretin.

Tar compounds with proven efficacy include crude coal tar, liquor carbonis detergens and anthralin.

Antibacterial agents that are effective in killing staphylcoccus, streptococcus and propionobacterium species often produce a therapeutic effect on papulosquamous and eczematous diseases. These include tetracycline, erythromycin, clindamycin, bacitracin, neomycin, chlorhexidine, sulfacetamide, meclocycline, polymixin, colistin and chloramphenicol.

Background information relating to the substances utilized in the present invention is as follows.

Artemisinin (Qinghaosu) and its analogs are the treatments of choice for cerebral or chloroquine resistant malaria or for patients with chloroquine allergy. Artemisinin is a naturally occurring substance, obtained by purification from sweet wormwood, Artemisia Annua. Artemisinin and its analogs are sesquiterpene lactones with a peroxide grouping, and are characterized by very low toxicity and poor water solubility. Artemisinin is known as a humoral immunosuppressive agent which is less active than cyclophosphamide, the latter being one of the major chemotherapeutic agents for carcinomas. Artemisinin stimulates cell-mediated immunity, and yet decreases abnormally elevated levels of polyamine regulatory proteins. It also markedly inhibits nucleic acid and protein syntheses. Further, it affects cellular membrane function and decreases hepatic cytochrome oxidase enzyme system activity. Still further, it is virustatic against influenza and cidal against three groups of pathogenic parasites.

Known analogs of artemisinin which have higher solubility in water are dihydroartemisinin, artemether, artesunate, arteether, propylcarbonate dihydroartemisinin and artelinic acid. Dihydroartemisinin has an antimalarial potency which is 60% higher than that of artemisinin. Artemether and artesunate have antimalarial potencies which are 6 times and 5.2 times, respectively, that of artemisinin. In terms of their ability to inhibit nucleic acid synthesis, dihydroartemisinin, artemether, artesunate, arteether, and propylcarbonate dihydroartemisinin all have 100 times the activity of artemisinin, and protein synthesis is stimulated to an even greater extent by these compounds. Artesunate stimulates the immune system at low doses and inhibits it at high doses. Artelinic acid is the most water-soluble and the most stable of the group. Two of the compounds in this group have been demonstrated to display synergistic activity with doxorubicin (a chemotherapeutic agent) and miconazole (an antifungal agent) in the in vitro killing of Plasmodia Falciparum, the etiologic agent of malaria.

The very low toxicity of these compounds to humans is a major benefit. Artesunate, for example, is twice as safe as artemether and only one-fiftieth as toxic as chloroquinine, the most common antimalarial. The first manifestation of toxicity of these compounds is generally a decreased reticulocyte count. Other manifestations include transient fever, decreased appetite and elevated blood transaminase levels, the latter an indication of hepatotoxicity.

Monocarboxylic acids and their ester and amide analogs are known to inhibit mitochondrial respiratory enzymes of Ehrlich tumor cells in mice. The monoglyceride ester of lauric acid (monolaurin) is particularly effective in inhibiting these enzymes. Monolaurin has potent cytotoxic activity against two leukemia cell lines and stimulates cell mediated immunity. These fatty acids and analogs significantly inhibit human pathogenic virus, fungi, yeast, and gram-positive bacteria growth. Monolaurin is the most potent as a microbial inhibitor. These compounds also are selectively absorbed by abnormally hyperactive cells. They have very low systemic toxicity and are mildly irritating topically to humans. Derivatives of 12-carbon atom length acids, especially monolaurin, have exceptional skin cell and stratum corneum penetration enhancing functions as well as stabilizing activity for other pharmaceutically active compounds.

SUMMARY OF THE INVENTION

It has been discovered that compounds having structures which contain sesquiterpene groups, of which artemisinin and its analogs are examples, when combined with monocarboxylic acids, esters or amides, are effective treatments for papulosquamous skin diseases, including psoriasis, and eczematous skin diseases, including seborrheic and atopic dermatitis.

The sesquiterpene compounds which are discovered to have these properties in accordance with this invention are compounds having a sesquiterpene structure, particularly an oxygenated tricyclic sesquiterpene structure with an endoperoxide group, and preferably those which are sesquiterpene lactones or alcohols, carbonates, esters, ethers and sulfonates thereof. Examples of such compounds include artemisinin; dihydroartemisinin; carbonate, sulfonate, ester and ether derivatives of dihydroartemisinin, notably artemether, arteether, artesunate and artesunate salts, and dihydroartemisinin propyl carbonate; and the bis-ether artelinic acid.

The monocarboxylic acids useful in combination with the sesquiterpene compounds, as either the acids themselves, esters or amides of the acids, are those of 5 to 19 carbon atom length, inclusive. These include straight-chain and branched-chain species, and saturated and unsaturated species, including species with multiple unsaturation sites. The present invention also extends to formulations of the above combination which further include any of the glucocorticosteroids, chemotherapeutic agents, retinoids, antibiotics, tars or antibacterial agents referred to above, as a means of further enhancing clinical efficacy.

DETAILED DESCRIPTION OF THE INVENTION AND PREFERRED EMBODIMENTS

Preferred embodiments of the present invention involve the use of sesquiterpene compounds having one of the following structural formulas:

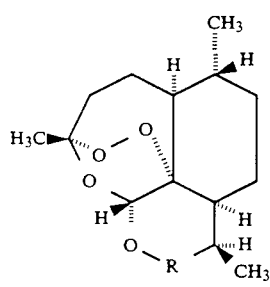

(I)

and

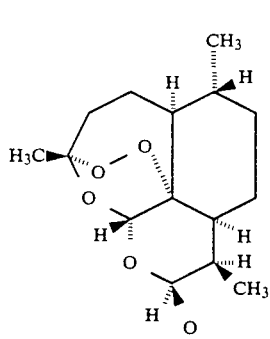

(II)

and

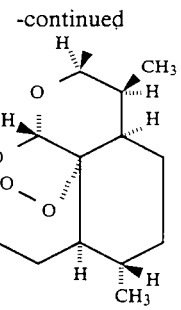

The symbol R in Formula I represents

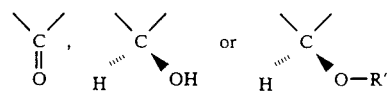

where R' is one of the following: alkyl,

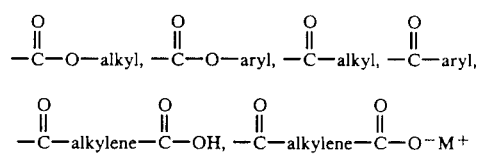

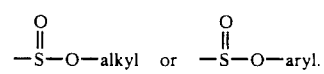

in which M is sodium or potassium, $$-\overset{O}{\underset{\|}{S}}-O-alkyl \quad or \quad -\overset{O}{\underset{\|}{S}}-O-aryl.$$

In the R' definition, the terms "alkyl" and "alkylene" preferably refer to lower alkyl and alkylene groups, notably $C_1$-$C_6$, with $C_1$-$C_4$ most preferred. Straight-chain and branched-chain groups are included, with straight-chain groups preferred. The term "aryl" preferably refers to phenyl and benzyl, with phenyl the most preferred. The symbol M refers to an alkali or alkaline earth metal, preferably sodium or potassium, with sodium the most preferred.

Preferred groups for R' are as follows: ($C_1$-$C_4$alkyl),

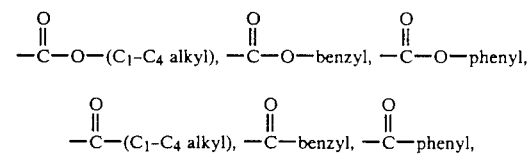

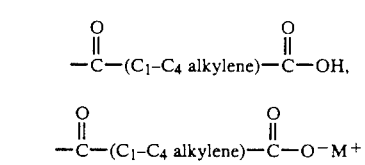

in which M is sodium or potassium,

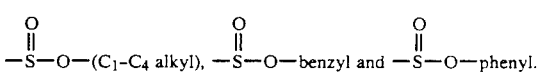

Further preferred R' groups are

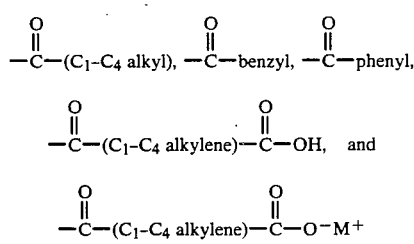

in which M is sodium or potassium.

The Formula I compound in which R is —C(=O)— is known by the common name artemisinin, and the one in which R is —CH(OH)— is dihydroartemisinin.

The Formula I compound in which R is —CH(OR′)— where R′ is —C(O)—(CH$_2$)$_2$—CH$_2$H is known by the common names artesunic acid and artesunate, the one where R′ is —C(O)—(CH$_2$)$_2$—CO$_2^-$Na$^+$ is known as sodium artesunate, the one where R′ is CH$_3$ is artemether, and the one where R′ is C$_2$H$_5$ is arteether.

The Formula II compound is known as artelinic acid.

Preferred monocarboxylic acids, esters and amides for use in combination with the sesquiterpenes of the present invention are those derived from straight-chain aliphatic acids, either saturated or unsaturated, of 9 to 18 carbon atom length. Examples include pelargonic, capric, undecanoic, lauric, tridecanoic, myristic, myristoleic, palmitic, palmitoleic, hexadecanoic, oleic, linoleic, linolenic, and octadecanoic acids.

Esters of these acids include glycerides and polyglycerides such as monoglycerides, triglycerides, hexaglycerides, and decaglycerides, as well as esters formed from methanol, ethanol, propylene glycol, polyethylene glycol, and sorbitol, and saccharides such as sucrose. Specific examples of esters are 1-monolaurin (generally referred to herein as "monolaurin"), 2-monolaurin, monocaprin, monomyristin, monolinolein; triglycerol caprylate, pelargonate, caprate, and laurate; hexaglycerol caproate, caprylate, pelargonate, caprate and laurate; decaglycerol butyrate, caprylate, pelargonate, caprate, and laurate; sucrose caprylate, caprate, laurate, myristate, palmitate, elaidate, oleate, and linoleate. Examples of amides are capratoyl-N,N-dimethylamide, lauryl-N,N-dimethylamide, myristoleyl-N,N-dimethylamide, laury-N,N-dimethylamide, myristoleyl-N,N-dimethylamide, and palmitoleyl-N,N-dimethylamide. The preferred amide is lauryl-N,N-dimethylamide.

The concentrations of the sesquiterpene structure compounds in the formulations to be applied in the practice of the present invention are not critical and may vary widely. In most applications, however, best results will be obtained using formulations containing the compounds at levels of from abut 0.01% to about 35% by weight, preferably from about 0.25% to about 10%. The amount of the compound actually administered for treatment will be a therapeutically effective amount, which term is used herein to denote the amount needed to produce a substantial clinical improvement. Optimal amounts will vary with the method of administration, and will generally be in accordance with the amounts of conventional medicaments administered in the same or a similar form. Topical application, for instance, is typically done from once to three times a day.

The fatty acids, esters and amides are likewise non-critical in terms of their concentration. Best results in most cases are generally achieved with concentrations within the range of about 0.025% to about 35% by weight, preferably about 1% to about 15% by weight.

The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and Azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

The amounts of each of these various types of additives will be readily apparent to those skilled in the art, optimal amounts being the same as in other, known formulations designed for the same type of administration. Stratum corneum penetration enhancers, for example, will typically be included at levels within the range of about 0.1% to about 15%.

The optimal systemic formulation of the basic combination of the present invention, i.e., the combination of sesquiterpene lactone and monocarboxylic acid (or derivative), may vary from one such combination to the next.

For the sesquiterpene artemisinin, preferred dosages are 1,100mg to 13,200mg in divided 12-hour doses administered over 3 to 6 days. A dosage of 4,400mg over a 5-day period is particularly preferred. For artemether, the preferred dosage range is 160mg to 2,880mg over 5 to 10 days, whereas a particularly preferred dosage is 480mg over 5 days administered intravenously. Arteether is preferably administered either intramuscularly or intravenously. Preferred dosages range from 100mg to 1,000mg, administered in divided doses over a period of 3 to 6 days.

The oral or systemic dosage of monolaurin ranges from 150 mg to 1800mg per day, administered in one, two or three divided doses.

The formulations of the present invention may further include as optional ingredients one or more agents already known for their use in the therapy of papulosquamous and eczematous diseases, for added clinical efficacy. Such combinations will in some cases provide added benefit. As mentioned above, these agents include glucocorticosteroids, chemotherapeutic agents, retinoids, antibiotics, tars and antibacterial agents. Appropriate amounts in each case will vary with the particular agent, and will be either readily known to those skilled in the art or readily determinable by routine experimentation.

The foregoing is offered primarily for purposes of illustration. Modifications, substitutions and variations on the materials and procedures described herein which will be readily apparent to those skilled in the art, may be made without departing from the spirit and scope of the invention.

What is claimed is:

1. A method for the treatment of a subject suffering a disease condition selected from papulosquamous and eczematous diseases, said method comprising administering to said subject a therapeutically effective amount of a combination of:

(a) a compound containing an oxygenated tricyclic sesquiterpene structure containing an endoperoxide group, and (b) a compound selected from the group consisting of $C_5$–$C_{19}$ monocarboxylic acids and esters and amides thereof.

2. A method in accordance with claim 1 in which compound (a) is a member selected from the group consisting of sesquiterpene lactones and alcohols, carbonates, esters, ethers and sulfonates thereof.

3. A method in accordance with claim 1 in which compound (a) is one having the formula

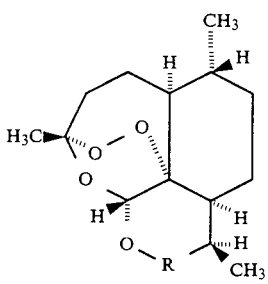

in which R is a member selected from the group consisting of

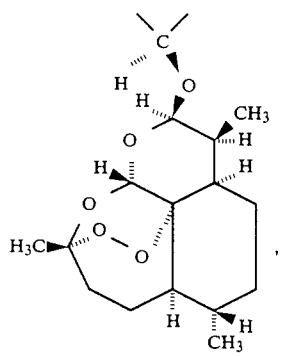

where R' is a member selected from the group consisting of alkyl,

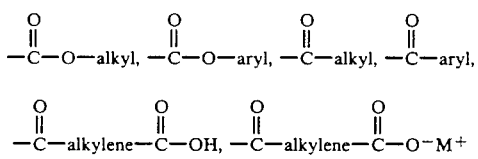

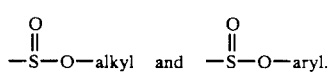

in which M is sodium or potassium, $$-\overset{O}{\underset{\|}{S}}-O-\text{alkyl} \quad \text{and} \quad -\overset{O}{\underset{\|}{S}}-O-\text{aryl}.$$

4. A method in accordance with claim 1 in which compound (a) is one having the formula

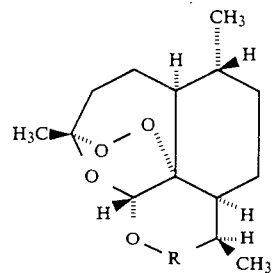

in which R is a member selected from the group consisting of

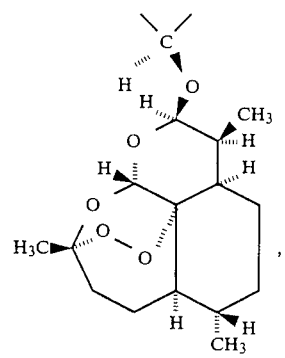

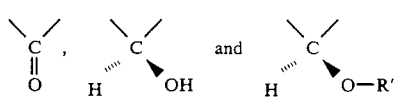

where R' is a member selected from the group consisting of $C_1$–$C_4$ alkyl,

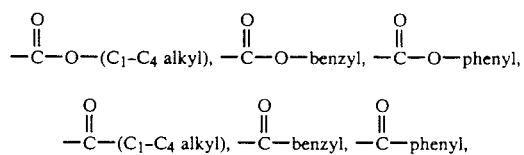

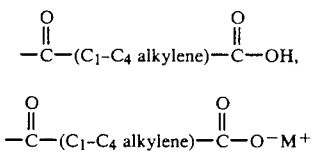

in which M is sodium or

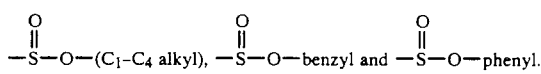

5. A method in accordance with claim 4 in which R' is a member selected from the group consisting of

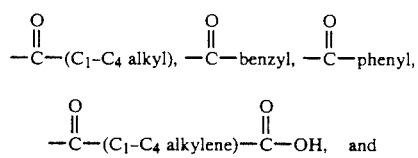

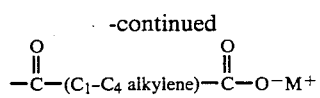

in which M is sodium or potassium.

6. A method in accordance with claim 1 in which compound (a) is one having the formula

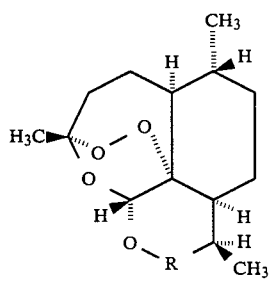

in which R is a member selected from the group consisting of

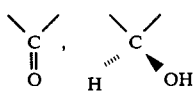

and esters, ethers, carbonates and sulfates of those in which R is

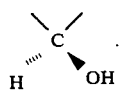

7. A method in accordance with claim 4 in which R is a member selected from the group consisting of

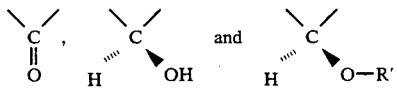

where R' is a member selected from the group consisting of

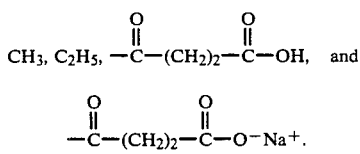

8. A method in accordance with claim 1 in which compound (a) is a member selected from the group consisting of artemisinin, dihydroartemisinin, artemether, arteether, artesunate, artelinic acid and dihydroartemisinin propyl carbonate.

9. A method in accordance with claim 1 in which compound (a) is artesunate.

10. A method in accordance with claim 1 in which compound (b) is a member selected from the group consisting of $C_9$–$C_{18}$ monocarboxylic acids, and sucrose esters, glycerol esters, and methyl amides thereof.

11. A method in accordance with claim 1 in which compound (b) is a member selected from the group consisting of lauric acid, monolaurin, and lauryl dimethylamide.

12. A method in accordance with claim 1 in which compound (b) is a member selected from the group consisting of monolaurin and lauryl-N,N-dimethylamide.

13. A method in accordance with claim 1 in which compound (a) is one having the formula

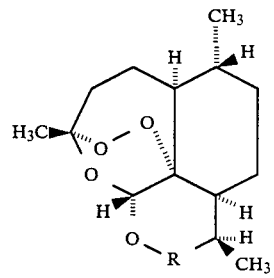

in which R is a member selected from the group consisting of

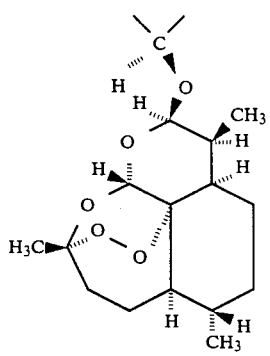

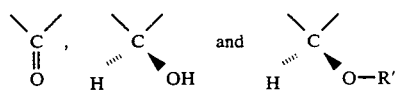

where R' is a member selected from the group consisting of $C_1$–$C_4$ alkyl,

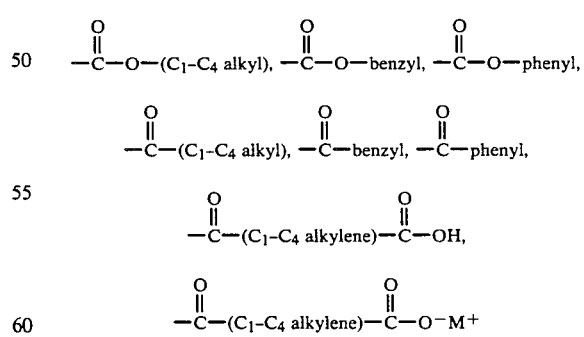

in which M is sodium or potassium,

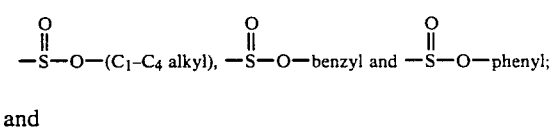

and compound (b) is a member selected from the group consisting of $C_9$–$C_{18}$ monocarboxylic acids, and sucrose esters, glycerol esters, and methyl amides thereof.

14. A method in accordance with claim 1 in which compound (a) is one having the formula

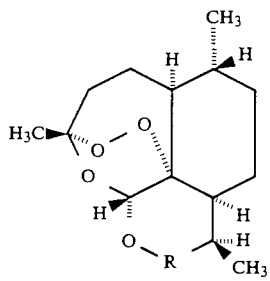

in which R is a member selected from the group consisting of

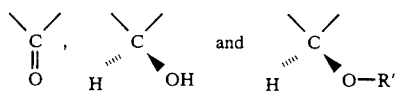

where R' is a member selected from the group consisting of $CH_3$, $C_2H_5$,

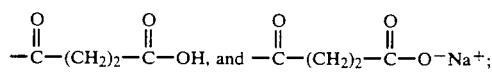

and compound (b) is a member selected from the group consisting of lauric acid, monolaurin, and lauryl dimethylamide.

15. A method in accordance with claim 1 in which compound (a) is a member selected from the group consisting of artemisinin, dihydroartemisinin, artemether, arteether, artesunate, artelinic acid and dihydroartemisinin propyl carbonate; and compound (b) is a member selected from the group consisting of monolaurin and lauryl-N,N-dimethylamide.

16. A method in accordance with claim 1 in which said disease condition is selected from the group consisting of psoriasis, lichen planus, pityriasis, parapsoriasis, seborrheic dermatitis, atopic dermatitis, contact allergic or irritant dermatitis, dyshidrosis, lichen simplex chronicus, eczema cracquelé, and cutaneous T cell lymphoma patch and plaque stages.

17. A method in accordance with claim 1 in which said disease condition is selected from the group consisting of psoriasis, seborrheic dermatitis, and atopic dermatitis.

18. A method in accordance with claim 1 comprising administering to said subject a formulation comprising from about 0.01% to about 35% by weight of compound (a), and from about 0.25% to about 35% by weight of compound (b).

19. A method in accordance with claim 1 comprising administering to said subject a formulation comprising from about 0.025% to about 10% by weight of compound (a), and from about 1% to about 15% by weight of compound (b).

20. A method in accordance with claim 1 in which said combination further comprises a member selected from the group consisting of glucocorticosteroids, chemotherapeutic agents, retinoids, antibiotics, tars and antibacterial agents.

21. A method in accordance with claim 1 comprising administering said combination systemically by oral, intramuscular or intravenous administration.

* * * * *